(12) United States Patent
Orduna Reyes et al.

(10) Patent No.: US 10,551,335 B2
(45) Date of Patent: Feb. 4, 2020

(54) HYDROCARBON SALINITY MEASUREMENT SYSTEM AT BOTTOM OF WELL AT EXTREME CONDITIONS OF PRESSURE AND TEMPERATURE BY MEANS OF TIME DOMAIN REFLECTOMETRY

(71) Applicant: INSTITUTO MEXICANO DEL PETROLEO, Mexico City (MX)

(72) Inventors: Ernesto Orduna Reyes, Mexico City (MX); Jose Manuel Dominguez Esquivel, Mexico City (MX); Jose Garcia Y Garcia, Mexico City (MX)

(73) Assignee: Instituto Mexicano del Petroleo, Mexico City (MX)

( * ) Notice: Subject to any disclaimer, the term of this patent is extended or adjusted under 35 U.S.C. 154(b) by 0 days.

(21) Appl. No.: 15/476,442

(22) Filed: Mar. 31, 2017

(65) Prior Publication Data

US 2017/0284952 A1 Oct. 5, 2017

(30) Foreign Application Priority Data

Mar. 31, 2016 (MX) .......................... a/2016/004131

(51) Int. Cl.
*G01N 27/06* (2006.01)
*G01N 33/28* (2006.01)

(52) U.S. Cl.
CPC ......... *G01N 27/06* (2013.01); *G01N 33/2835* (2013.01)

(58) Field of Classification Search
CPC ........................... G01N 27/06; G01N 33/2835
See application file for complete search history.

(56) References Cited

U.S. PATENT DOCUMENTS

| 3,783,057 A | * | 1/1974 | McNerney | ............. | H02G 1/145 |
| | | | | | 156/49 |
| 4,268,371 A | * | 5/1981 | Brun | ........................ | H01B 7/24 |
| | | | | | 204/196.33 |

(Continued)

*Primary Examiner* — Christopher P McAndrew
*Assistant Examiner* — Zannatul Ferdous
(74) *Attorney, Agent, or Firm* — Jason P. Mueller; Adams and Reese LLP

(57) ABSTRACT

The object of the present invention relates to a system for measuring the salinity of hydrocarbons at the bottom of an oil well, using the technique of time domain reflectometry (TDR). The system comprises an electromagnetic pulse generator, an oscilloscope for displaying and measuring the frequency, amplitude and wavelength of the signal, a signal amplifier, a computer for processing and storing the information, and a metal wire that functions as a waveguide To transmit the signal from the signal generator to the hydrocarbon to which its salinity is to be determined at the bottom of the well. The signal returns from the bottom of the well to the oscilloscope where the difference between the sent signal and the return signal is measured. This difference allows us to infer the salinity of the hydrocarbon. The guide wire is attached to the production line by means of a strap or other fastening device from the surface to the bottom of the well, where the tip of the cable is inserted into the pipe to contact the hydrocarbon and in this way detect its salinity. It is possible to use the same pipe as a waveguide to transmit the test signal to the bottom of the well. In addition, the salinity of the hydrocarbon can be determined at different points along the well.

8 Claims, 7 Drawing Sheets

(56) References Cited

U.S. PATENT DOCUMENTS

| | | | |
|---|---|---|---|
| 5,376,888 A * | 12/1994 | Hook | G01N 22/04 |
| | | | 324/533 |
| 6,114,857 A | 9/2000 | Kohl | |
| 8,912,806 B2 | 12/2014 | Banks et al. | |
| 2004/0100273 A1 | 5/2004 | Liney et al. | |
| 2008/0015792 A1 * | 1/2008 | Scott | G01N 22/00 |
| | | | 702/25 |
| 2008/0265654 A1 * | 10/2008 | Kearl | E21B 43/2401 |
| | | | 299/14 |
| 2014/0085133 A1 | 3/2014 | Flasza et al. | |
| 2016/0320516 A1 * | 11/2016 | Clark | G01V 3/24 |

* cited by examiner

HYDROCARBON SALINITY MEASUREMENT SYSTEM AT BOTTOM OF WELL AT EXTREME CONDITIONS OF PRESSURE AND TEMPERATURE BY MEANS OF TIME DOMAIN REFLECTOMETRY

TECHNICAL FIELD OF THE INVENTION

The present invention relates to a salinity measuring system at the bottom of an oil well, using the time domain reflectometry (TDR) technique. The system comprises an electromagnetic pulse generator, an oscilloscope for displaying and measuring the frequency, amplitude and wavelength of the signal, a signal amplifier, a computer to process and store information and a metal cable that functions as a waveguide to transmit the signal from the signal generator to the hydrocarbon to which its salinity at the bottom of the well is to be determined. The signal returns from the bottom of the well to the oscilloscope where the difference between the sent signal and the return signal is measured. This difference allows us to infer the salinity of the hydrocarbon. The guide wire is attached to the production line by means of a strap or some other fastening device from the surface to the bottom of the well, where the tip of the cable is introduced to the pipe to get in contact with the hydrocarbon and in this way to detect its salinity. It is possible to use the same pipe as a waveguide to transmit the test signal to the bottom of the well. Additionally, the salinity of the hydrocarbon can be determined along the well.

It is important to note that at present, there are no companies in the market that can offer a sensor or technique capable of measuring salinity to very particular conditions of bottom of well, Therefore, the development of this type of measurement system will provide relevant information to optimize the production in producing wells and to support during the tests of injection of thermal fluids in oil fields both on land and offshore in marine zone, For improved recovery of hydrocarbons.

Commercial salinity sensors only operate at normal pressure conditions, ie at atmospheric pressure and ambient temperature conditions. Salinity sensors for application in the industry, Cannot be applied under the background requirements of an oil production well as it operates with liquids and gases at a pressure of approximately 350 kg/cm2, with temperatures of up to 150° C. at depths of 5,000 m in the presence of sulfuric acid, so the main problem is pressure, temperature and corrosion.

The advantage of this invention is that this metering system is able to withstand the abovementioned extreme conditions at the bottom of a hydrocarbon well in naturally fractured deposits in order to determine the characteristics and quality of the hydrocarbon to optimize the process of production.

This system also allows us to determine changes in salinity at different points along the well, due to changes in the hydrocarbon or the invasion of water from a nearby aquifer.

BACKGROUND OF THE INVENTION

The Time domain reflectometry have been for many years and remain the fastest and most accurate instruments for detecting the structural problems of wiring. TDRs are used to locate and identify faults on any type of twisted cables and coaxial cables.
The uses of TDR are as follows:
Locate faulty fittings.
Locate unknown splices.
Find components on the line.
Locate water or moisture in the cable.
Assistance in the measurement and verification of new cable reels.
Locate holes or damage to the cables.
To document the integrity of the wiring.
To document or map wired networks.
Principles of Operation The TDR works with the same radar principle. A pulse of energy is transmitted through the wire to be tested, and when the pulse reaches the end of the wire, or a fault along this, part or all of the pulse energy is reflected towards the instrument.

The TDR measures the time it takes for the signal to travel on the cable, between the instant the signal was sent and the instant it received the signal reflected by the point of discontinuity, this time converts it to a distance and shows the magnitude of discontinuity.

TDR analysis generally does not detect capacity isolated devices or inductive. In such cases the TDR scan is complemented by a detailed high frequency evaluation and a physical inspection.
Impedance The TDR identifies changes in cable impedance that may be caused by a variety of circumstances, including cable damage, water ingress, changes in cable type, improper installation, and any manufacturing defects.

The insulation material that holds the conductors apart is called dielectric and the impedance of the wire is determined by the spacing between the conductors and the type of dielectric used.

The reflection of the pulse sent by the TDR to the cable, is produced by a change of Impedance along the cable and these changes are what determine the amplitude of the reflection.
The Width of the Pulse Many TDRs have selectable pulse widths, and the higher the pulse, the more energy is transmitted to the wire. The pulse widths used are: 2 ns, 10 ns, 100 ns, 1000 ns, 2000 ns, and 4000 ns. According to the TDR model you can include all or just a few pulse widths.

If the fault is very small, the energy of a small pulse may not be enough to travel through the wire, see the fault and that the reflected pulse travel back, this added to the attenuation of the wire, can cause the detection of this fault becomes a bit difficult. In this case the energy should be increased so that the fault can be appreciated.

Las formas de onda de los pulsos mostrados en las figuras muestran los cambios en estas, al solo cambiar el ancho del pulso (con el mismo cable y las mismas configuraciones del TDR).

The need to know the salinity of the hydrocarbons is due to the fact that this salinity indicates many characteristics and properties of the hydrocarbon such as: its origin related to the salinity of the associated congenital water, the connectivity of the different wells in a field, the effects of the Salinity in the viscosity and fluidity of the hydrocarbon, the variation of the salinity by the physical and chemical changes of the hydrocarbon when varying the pressure and the temperature, the invasion of aquifers of fresh or salt water towards the well, among others. This information is very important for well completion in order to improve and optimize production. In addition to the need to incorporate reserves, there is the cost of high oil prices, which motivate the application of new technologies for improved recovery of hydrocarbons. Within these technologies is the improved recovery process by injection of thermal fluids mixed with catalysts to promote an in situ reaction. Pemex Exploration and Production currently documents these types of tests to be applied in offshore and offshore fields (fractured carbonate sites).

The TDR technique has been widely used to detect faults in electrical transport cabling systems, computer network systems and electronic telecommunication systems. Research is currently underway to apply this technology in the detection of leaks in tanks and pipelines, for application in industry and to determine soil moisture, for application in agriculture (nurseries and fields). In these cases it is not required to have as much accuracy of the return signal to determine the location and magnitude of the fault that is normally a short circuit or an open circuit. However, to perform the measurement of some variable (such as salinity) by the TDR method, a high accuracy is required in the equipment that records the return signal, which in this case is the oscilloscope, not only to detect the presence Of salt in the fluid, but to quantify the amount of salt and to make a reliable measurement.

However, because of the accuracy required to quantify the TDR return signal, this technology has not been commercially applied under standard conditions to ambient temperature and pressure, much less to downhole conditions.

Doing a patent search that could be related to our invention, we find the following:

The U.S. Pat. No. 6,114,857A dated Sep. 5, 2000, entitled "System and Method for Monitoring Corrosion in Oilfield Wells and Pipeline Utilizing Time Domain Reflectometry". A system for measuring and controlling corrosion in oil well production pipelines at well bottom conditions is described.

In our invention, although the conditions of pressure and temperature at the bottom of the well could be similar, the objective and operation of the system are completely different, both in the conditions of the signal sent by the signal generator, and in the form and interpretation of the response signal. In this case the corrosion is measured and in our case salinity is measured that have completely different behaviors.

The U.S. Pat. No. 8,912,806B2 dated Dec. 16, 2014, entitled "Method of Cutting and Testing a Pipeline Cut Under Water or Under Seabed". A system based on Time Domain Reflectometry (TDR) is described, It can be determined when a pipe has been cut completely when work is done deep well or on the seabed. In this technology, electromagnetic signals are sent through the pipeline and returned to the TDR signal analyzer. These signals are different when the pipe is complete and when it is broken.

As can be seen, the aim of this invention and the present invention is completely different, as are the signals and the interpretation thereof.

The patent US20040100273A1, entitled "Testing Electrical Integrity of Electrically Heated Subsea Pipelines", refers to a method where electrical connectivity is tested by Time Domain Reflectometry (TDR) of a heating system of the pipes coming from the Wells and cross the seabed to the surface. This heating of the pipes is required to prevent thermal shocks or cooling of the oil as it passes through the seabed.

This application differs from our invention in that, in this case, the TDR system only verifies the connectivity of the system to avoid open circuits or short circuits that affect the operation of the heating system, using the same pipe as a waveguide. In our case, the response signal in the TDR should not only identify a change in impedance but also quantify it to determine the salinity of the oil at the bottom of the well.

The patent US20140085133A1, entitled "Time Domain Reflectometry Based Method for Emulsion Detection and Profiling", relates to a method by which the presence and location of an emulsion at an interface which may be liquid and gas (water and air) or Two non-miscible liquids (water and oil), in this way the level of liquid in a tank can be measured.

The difference with our invention is that these tests to determine the location of the emulsions are carried out under conditions of pressure and ambient temperature, however, in our invention, the test conditions are well bottomed.

BRIEF DESCRIPTION OF THE FIGURES OF THE INVENTION

For the purpose of providing an accurate description of the depth salinity sensor of the well, its components, the waveguide installation alternatives and the interpretation of the response signal that it may have, reference will be made to the following Figures.

Figure 1:
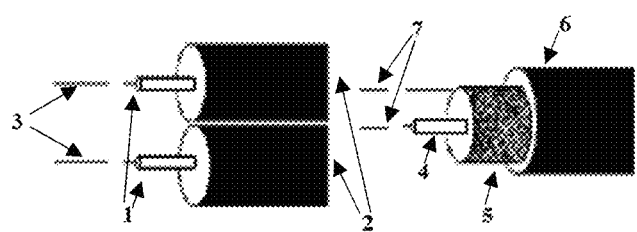
FIG. 1 shows examples of cables as waveguides, firstly two parallel metal conductors (1), separated by an insulator (2), a regular distance (3). The other in a concentric coaxial cable, where its metallic conductors (4) (5), with their insulating cover (6) and separated by a constant distance (7).
Figure 2:
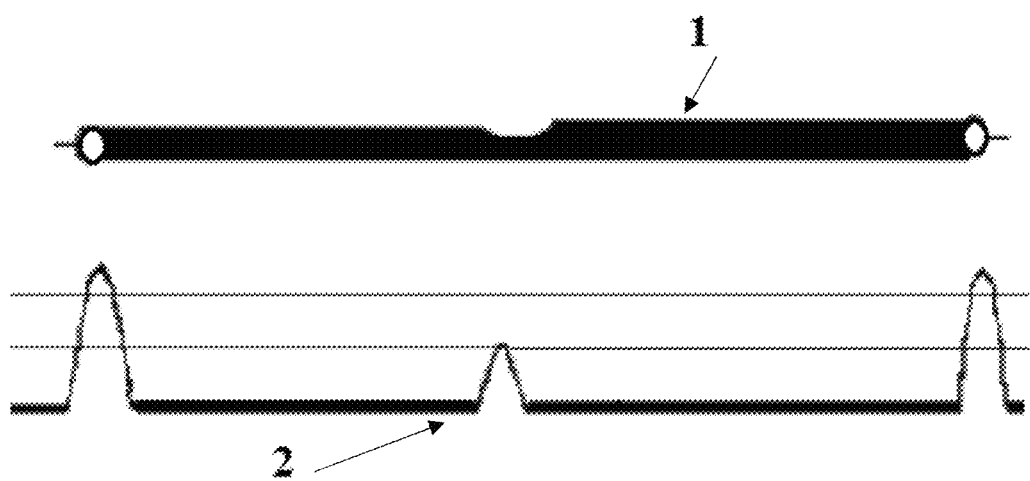
FIG. 2 shows an example of the application of the TDR for the detection of faults in electric cables (1), in the graph (2) the discontinuity or failure in the cable produces a change in the sent waveform, where Type of fault and the location of this.
Figure 3:
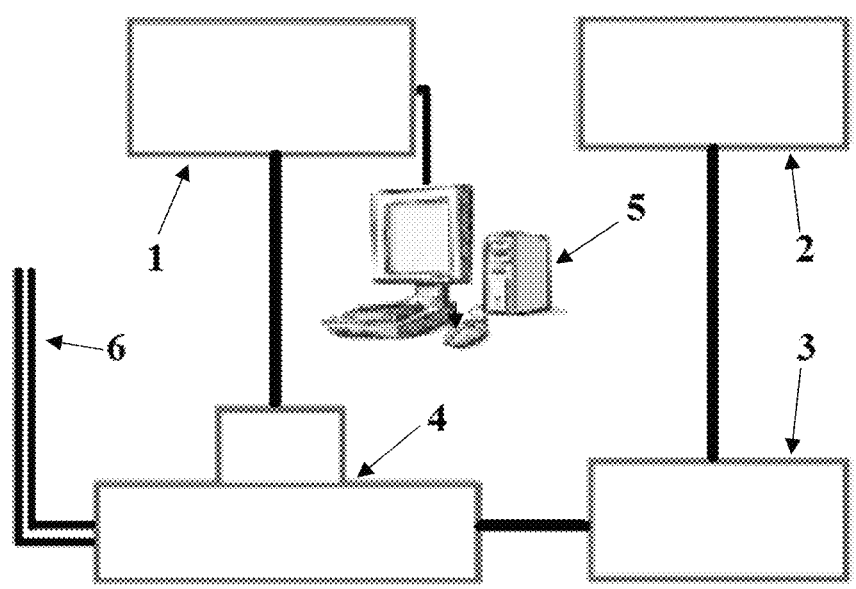

In FIG. 3, the implementation of a laboratory TDR consisting of an oscilloscope (1), a pulse generator (2), an amplifier (3), a signal adapter (4), an acquisition system, Data analysis and storage (5) and finally the waveguide (6).

Figure 4:
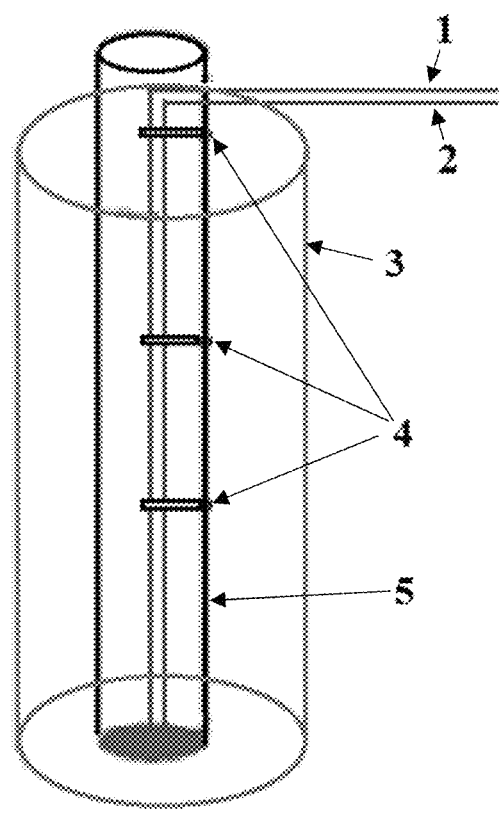

FIG. 4 shows how the waveguide (1), (2) would be installed inside an oil well (3) to determine the amount of salinity in real time, in this case the waveguide of metal cables (1) (2) is fixed by means of insulating fasteners (4) to the production pipe (5), so as not to bring the wave guide (1), (2) and the production pipe (5) into contact, which is also Metal.

Figure 5:
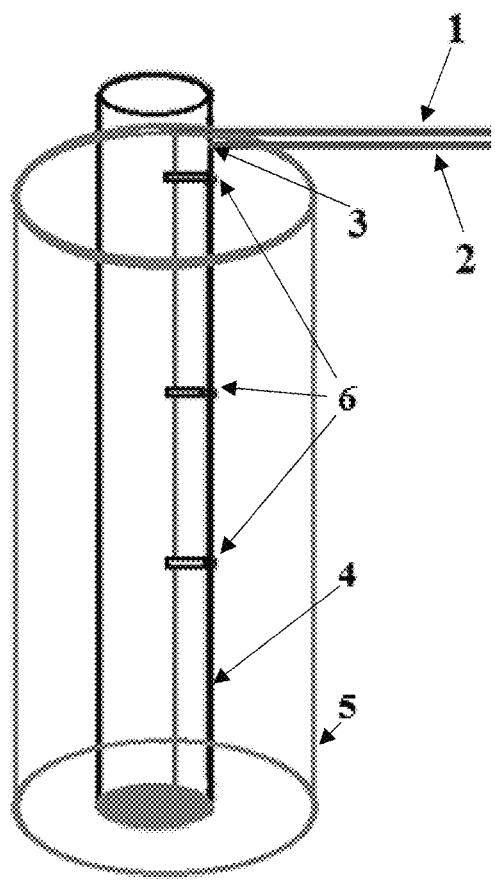

FIG. 5 shows another option of installing the waveguide (1), (2), the point of attachment (3) of one of the metal cables to the production line (4), into an oil well (5), By means of insulating fasteners (6), in this case the production line (4) will be one of the conductors of the waveguide (1), (2) inside the oil well (5), both the cable and the pipe Act as the waveguide, and this waveguide arrangement will be the means for transmitting the pulse sent by the TDR to the bottom of the well.

Figure 6:
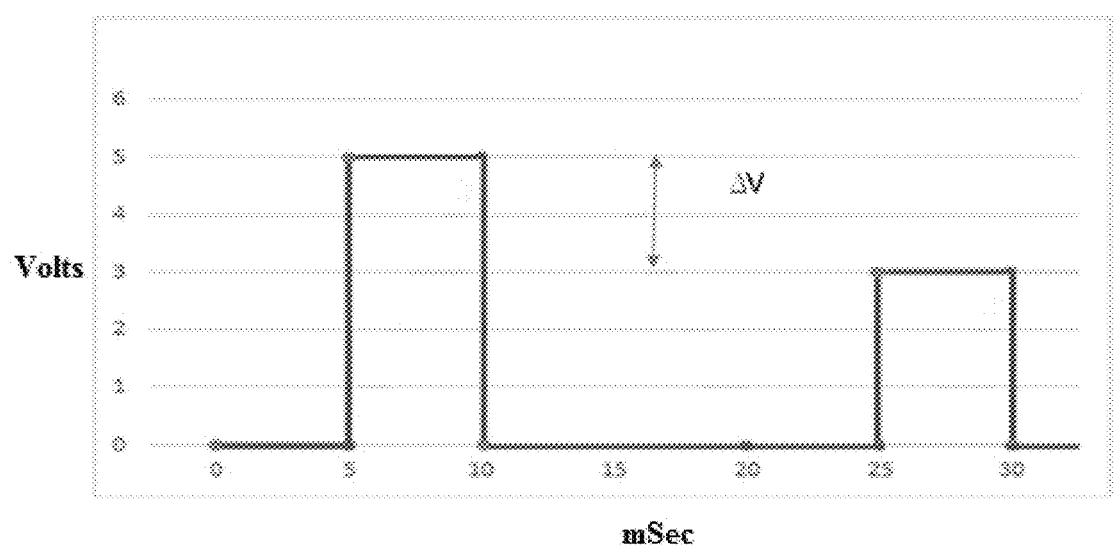

In FIG. 6, it presents the graph of a pulse sent to the bottom of the well through a waveguide, as well as the shape of the return pulse signal. It can be observed as there is a decrease in the amplitude (voltage) due to the presence of salt when the cable is put in contact with the crude. By quantifying the voltage decrease the salinity of the crude can be determined.

Figure 7:
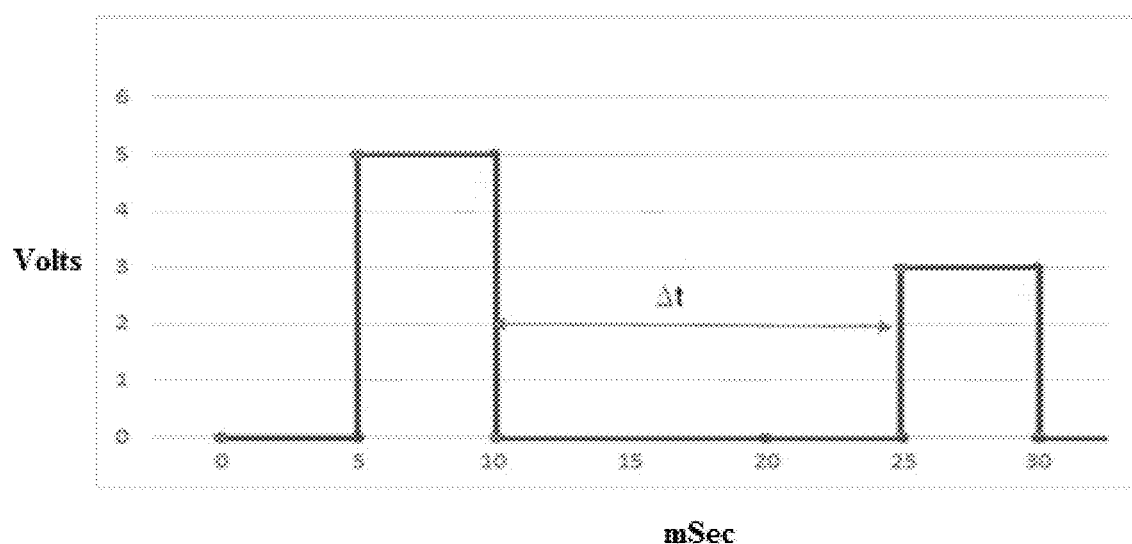

In FIG. 7, it shows the comparison between the shape of the pulse sent to the bottom of the well and the return signal. It can be seen that the return signal has a time delay. By quantifying this time delay and knowing the speed at which the signal travels in the guide wire, it is possible to determine the distance at which the disturbance occurs, ie the distance at which the salinity measurement is performed.

DETAILED DESCRIPTION OF THE INVENTION

The system for measuring salinity in wellbore hydrocarbons using the time domain reflectometry (TDR) technique is based on a pulse generator that sends a pulse through a waveguide or cable, This metal waveguide is brought into contact with the hydrocarbon at which its salinity is to be measured, the return signal is measured on an oscilloscope where it is compared to the originally sent pulse. The time of arrival and amplitude of the return pulse are reflections of the change in impedance change at several points or at the end of the line, these changes in the impedance can be measured and analyzed. Given a velocity of propagation of the pulse in the line, the arrival time of the return pulse depends on the location of the impedance change, whereas the amplitude of the return pulse is related to the attenuation of the signal in the cable due to the Length of said cable.

How to mentioned above, FIG. 4 shows how the waveguide (1) (2) would be installed inside an oil well (3) to determine the amount of salinity in real time, it is worth mentioning that one of the advantages of this system is that it can be subjected to extreme conditions of pressure and temperature, by the metallic composition of the waveguide. In this case, the waveguide of metallic cables (1), (2) is fixed by means of insulating fasteners (4) to the production pipe (5) so as not to contact the waveguide 1 (2)) And the production pipe (5) which is also metallic.

FIG. 6 shows an example of the type of signal obtained on the oscilloscope plotting time vs voltage, the first pulse on the left side is the pulse originally emitted by the pulse generator through the waveguide, the second pulse on the right side is the pulse returned or reflected, the difference in amplitude gives us the idea of the change in impedance change, which is directly related to the amount of salt contained in the hydrocarbon.

FIG. 7 as in FIG. 6 shows an example of the type of signal obtained on the oscilloscope plotting time vs voltage, the first pulse on the left side is the pulse originally emitted by the pulse generator through the waveguide, the second Pulse on the right side is the returned or reflected pulse, the difference in the return time of the second pulse tells us the distance at which the measurement was made.

There is a relationship between the amplitude of the pulse and the resolution of the return time of the pulse, which corresponds to the distance of the length that reaches the line or cable. For short cables, a narrow pulse is sufficient to give a high resolution of the time. When the cable is long, the amplitude of the effective band is considerably reduced. A tight pulse on a long wire experiences so much attenuation that the reflection becomes virtually undetectable. For this reason, long cables require larger pulses, which contain energy at low frequencies.

How to mentioned above, FIG. 3 of the present invention consists mainly of a pulse generator (2), the function of which is to generate pulse-type electromagnetic signals. The pulse generator must be capable of generating signals over a wide range of frequencies and wavelengths to determine with which values of these variables a perceptible change in the waveform of the return signal is observed with respect to the change in the Amount of salt in the hydrocarbon, in this way to be able to quantify its salinity. The signal sent by the signal generator upon return is attenuated due to the distance and the material with which the guide wire is constructed, this attenuation can be avoided or decreased by modifying the frequency, amplitude and voltage of the signal, up to Get the waveforms of the return signal that give us the most appreciable and reliable results possible. A range of pulse amplitudes ranging from a few nanoseconds to a few microseconds is used for measurements on short cables. The return voltage signal is plotted on the x-axis against the distance along the line under test. Relatively longer amplitude pulses, ranging from microseconds to milliseconds or more, have a fast time increment to provide power over a wide frequency spectrum, allowing measurements to be performed over a wide range of cable lengths. Even if the signal sent is calibrated at the appropriate frequency and amplitude to have a minimum attenuation as a function of distance and cable material, this minimum attenuation must be considered within the equation for transferring voltage and frequency in salinity and distance, for Get more accurate results.

Even if the signal sent is calibrated at the appropriate frequency and amplitude to have a minimum attenuation as a function of distance and cable material, this minimum attenuation must be considered within the equation for transferring voltage and frequency in salinity and distance, for Get more accurate results.

Another component of the system is an adjustable gain signal amplifier (3), which amplifies the return wave signal of the reflected wave received from the receiver. The gain of the adjustable gain amplifier can be made to be varied using the Technique of Time Variable Gain (TVG).

Another indispensable element in the system is a computer (5) for processing the information and storing the data. Digital voltage samples can be stored together with their corresponding acquisition time as elements of a data array in computer memory, for example, random access memory or the like, for post-processing or post-processing.

Alternatively, it may be sufficient to store the sampling periods in the computer to allow the acquisition time of the digitized voltage samples to be calculated from their position within the array. The computer presents the results of the analysis and post-processing to the user through the screen or a printer. In some designs it may be advantageous for the computer to incorporate synchronization and control functions of the time base generator.

The standard differentiation for raw data storage is performed numerically on the computer. The acquisition time of consecutive samples of digital voltage differs over a sampling period. The fixed preset time shift between two digital voltage samples corresponds to a difference in the array index between elements stored in a data array. The differentiation proceeds by a numerical subtraction of pairs of array elements whose indices are compensated for by a multiple sample integrator of the same period as the pre-set time offset. Using adaptive numerical differentiation the time shift varies in a systematic way. Adaptive numerical differentiation is developed in the computer by placing the travel time or its equivalent, the effective pulse amplitude at an initial shift time. Pairs of data array elements are selected such that the difference in acquisition times is equivalent to the effective pulse amplitude. Differentiation is obtained by taking the pairs of elements sequentially in the order in which they were obtained. The first element of the pair corresponding to the last time of the acquisition is numerically subtracted from the other element of the pair and the difference obtained is recorded in a sorted differentiated array. This is an advantage for choosing values for the time shift which is a multiple integrator of the sampling period. As the differentiation progresses through the data array, the time shift is gradually increased until an end time shift is reached, preferably until the acquisition time of the last element of the pair that has been subtracted corresponds to the distance of the Edge of the guide wire. Thus, the effective pulse amplitude is adjusted in the microprocessor at a distance from a change in reactance, increasing the time shift with the start time when the pulse is injected into the line under test by the pulse generator.

Finally we have a metal cable that goes from the signal generator to the bottom of the production well or observer well where the measurement (6) will be performed. This cable acts as a waveguide to transmit the electromagnetic signal from the signal generator to the bottom of the well and from the bottom of the well to the oscilloscope on the surface, where the waveform of the sent signal and the return waveform are displayed. The materials of commercial conductors that can be used as a guide for conducting the electric signal are any type of electrically conductive metal, such as copper, aluminum, iron and steel. The characteristics of these materials are described below: Copper has a high resistance to corrosion, a conductivity of 100% a speed of 66% of the speed of light, but a greater attenuation of the return signal at high frequencies (109 dB/100 m to 1000 MHz). The steel has a high mechanical strength, high resistance to high temperatures, has a low conductivity of 15%, a speed of 85% of the speed of light and a low attenuation of the signal at high frequencies (21.5 dB/100 m to 1000 MHz). Aluminum is a very light and economical material, has a conductivity of 65%, a speed of 60% of the speed of light, a signal attenuation at high frequencies of 48 dB/100 m to 1000 MHz. A material that can give very good results as a guide wire is copper-coated steel as it provides the high mechanical strength and resistance to high temperatures of the steel and the high conductivity of the copper. In addition, the same casing can be used as a waveguide for transmitting the test signal from the signal generator to the bottom of the well and the return of the signal to the oscilloscope where it is recorded and sent to the computer where it is analyzed and stored.

What is claimed is:

1. A system for measuring salinity of a hydrocarbon at a bottom of a hydrocarbon well by means of a time domain reflectometry technique, comprising:
    a waveguide or cable that is attached to, and in direct electrical contact with, a hydrocarbon production line at the bottom of the well and that is in contact with the hydrocarbon, wherein the waveguide or cable comprises materials suitable to withstand temperatures above 500° C. and pressures greater than 10,000 psi,
    an electromagnetic pulse generator connected to the waveguide or cable and configured to generate a test signal on the waveguide or cable,
    an oscilloscope configured to measure the test signal generated by the electromagnetic pulse generator and to measure a signal on the waveguide or cable that is reflected by the hydrocarbon at the bottom of the well,
    a signal amplifier and a signal adapter configured to control signal characteristics and pulse sharpness, and
    a processor circuit configured to control the electromagnetic pulse generator, the oscilloscope, the signal amplifier, and the signal adapter.

2. The system of claim 1, wherein:
the processor circuit is further configured to determine the salinity of the hydrocarbon based on characteristics of the test signal and the signal reflected by the hydrocarbon.

3. The system of claim 1, wherein:
the waveguide or cable comprises materials suitable to withstand a corrosive and abrasive environment.

4. The system of claim 1, wherein:
the electromagnetic pulse generator is configured to generate signals with variable voltage, frequency and wavelength ranges, and
the amplifier and signal adapter are configured to make measurements at lengths greater than 5000 meters without loss of signal and with accuracy and reliability.

5. The system of claim 1, wherein:
the hydrocarbon production line is configured to serve as the waveguide.

6. The system of claim 1, wherein:
the system is configured to measure salinity of hydrocarbons and brines in oil and geothermal wells.

7. A non-transitory computer readable storage device having computer program instructions stored thereon that, when executed by a processor, cause the process to perform operations comprising:
    controlling an electromagnetic pulse generator to generate a test signal on a waveguide or cable, wherein the waveguide or cable is attached to, and in direct electrical contact with, a hydrocarbon production line at a bottom of a hydrocarbon well and that is in contact with the hydrocarbon, and wherein the waveguide or cable comprises materials suitable to withstand temperatures above 500° C. and pressures greater than 10,000 psi;
    controlling an oscilloscope to measure the test signal generated by the electromagnetic pulse generator and to measure a signal on the waveguide or cable that is reflected by a hydrocarbon at the bottom of the hydrocarbon well; and
    controlling a signal amplifier and a signal adapter to control signal characteristics and pulse sharpness.

8. The non-transitory computer readable storage device of claim 7, further comprising computer program instructions that, when executed by a processor, cause the processor to perform operations comprising:
    analyzing and evaluating characteristics of the test signal and the signal that is reflected from the hydrocarbon, the characteristics including amplitude, voltage, and frequency;
    transforming the signals to determine correlations in time and distance; and
    determining salinity values based on the determined correlations.

* * * * *